US011497553B2

United States Patent
Reinhard et al.

(10) Patent No.: US 11,497,553 B2
(45) Date of Patent: Nov. 15, 2022

(54) DEVICE AND/OR METHOD FOR TREATING DISEASES OF THE SKIN, GLANDS, MUCOSAE, CONNECTIVE TISSUE, NERVES AND/OR HORNY TISSUE

(71) Applicant: Lenicura GmbH, Wiesbaden (DE)

(72) Inventors: Katharina Reinhard, Mainz (DE); Andreas Hafner, Mainz (DE); Arend Poppner, Essen (DE)

(73) Assignee: Lenicura GmbH

( * ) Notice: Subject to any disclaimer, the term of this patent is extended or adjusted under 35 U.S.C. 154(b) by 553 days.

(21) Appl. No.: 15/541,097

(22) PCT Filed: Nov. 28, 2015

(86) PCT No.: PCT/EP2015/002396
§ 371 (c)(1),
(2) Date: Jun. 30, 2017

(87) PCT Pub. No.: WO2016/107660
PCT Pub. Date: Jul. 7, 2016

(65) Prior Publication Data
US 2017/0340385 A1 Nov. 30, 2017

(30) Foreign Application Priority Data
Jan. 3, 2015 (DE) .......................... 102015000150.7

(51) Int. Cl.
*A61B 18/00* (2006.01)
*A61B 18/18* (2006.01)
(Continued)

(52) U.S. Cl.
CPC ............ *A61B 18/18* (2013.01); *A61N 5/0616* (2013.01); *A61B 2017/00747* (2013.01);
(Continued)

(58) Field of Classification Search
CPC .. A61B 18/18; A61B 2017/00747; A61N 5/00
See application file for complete search history.

(56) References Cited

U.S. PATENT DOCUMENTS 4,298,005 A * 11/1981 Mutzhas ................. H01J 61/52
359/359
6,702,808 B1 3/2004 Kreindel
(Continued)

FOREIGN PATENT DOCUMENTS

CN 203417405 U 2/2014
CN 103610498 A 3/2014
(Continued)

OTHER PUBLICATIONS

Van Der Lugt et al. (Feb. 17, 2009). A multicenter study of cellulite treatment with a variable emission radio frequency system. Retrieved Apr. 15, 2021 (Year: 2009).*
(Continued)

*Primary Examiner* — John R Downey
*Assistant Examiner* — Anant A Gupta
(74) *Attorney, Agent, or Firm* — Reising Ethington, P.C.

(57) ABSTRACT

The disclosure relates to a device and a method for the treatment of diseases of the skin, glands, mucousae, connective tissue, nerves and/or horny tissue. The device is adapted for the treatment of diseases of the skin, glands, mucousae, connective tissue, nerves and/or horny tissue and has at least one applicator, which applicator is arranged outside the device housing; at least one radio wave module, which radio wave module is adapted to generate an adjustable electromagnetic radiation with a variable frequency or with at least one constant frequency with an adjustable variable or at least one adjustable constant intensity.

13 Claims, 3 Drawing Sheets

(51) Int. Cl.
*A61N 5/06* (2006.01)
*A61N 1/40* (2006.01)
*A61B 17/00* (2006.01)
*A61N 5/00* (2006.01)

(52) U.S. Cl.
CPC .............. *A61B 2018/00458* (2013.01); *A61B 2018/1807* (2013.01); *A61N 1/40* (2013.01); *A61N 5/00* (2013.01); *A61N 5/0624* (2013.01); *A61N 2005/0635* (2013.01); *A61N 2005/0644* (2013.01); *A61N 2005/0659* (2013.01); *A61N 2005/0662* (2013.01); *A61N 2005/0667* (2013.01)

(56) References Cited

U.S. PATENT DOCUMENTS

| | | | |
|---|---|---|---|
| 6,889,090 | B2 | 5/2005 | Kreindel |
| 6,939,344 | B2 | 9/2005 | Kreindel |
| 7,041,100 | B2 | 5/2006 | Kreindel |
| 7,238,183 | B2 | 7/2007 | Kreindel |
| 7,643,883 | B2 | 1/2010 | Kreindel |
| 7,878,965 | B2 * | 2/2011 | Haber .................. A61N 5/0619 600/9 |
| 2002/0173780 | A1 | 11/2002 | Altshuler ............. A61B 18/203 606/90 |
| 2004/0225339 | A1 | 11/2004 | Yaroslavsky et al. |
| 2005/0049658 | A1 * | 3/2005 | Connors .............. A61B 18/203 607/88 |
| 2005/0214453 | A1 * | 9/2005 | Kawanishi ................ G02B 1/12 118/620 |
| 2006/0271028 | A1 | 11/2006 | Altshuler et al. |
| 2009/0012515 | A1 * | 1/2009 | Hoenig ................ A61B 18/203 604/20 |
| 2010/0069898 | A1 * | 3/2010 | O'Neil ................ A61B 18/203 607/90 |
| 2010/0305494 | A1 * | 12/2010 | Clements ................ A61L 2/084 604/20 |
| 2011/0015549 | A1 * | 1/2011 | Eckhouse ............ A61N 5/0616 601/3 |
| 2011/0190745 | A1 * | 8/2011 | Uebelhoer ........... A61B 18/203 606/9 |
| 2013/0066237 | A1 * | 3/2013 | Smotrich ............. A61N 5/0619 601/2 |
| 2013/0218243 | A1 * | 8/2013 | Schomacker ........ A61N 5/0613 607/101 |
| 2014/0052029 | A1 * | 2/2014 | Khen ...................... A61N 5/06 601/2 |
| 2017/0340385 | A1 | 11/2017 | Reinhard et al. |

FOREIGN PATENT DOCUMENTS

| | | | |
|---|---|---|---|
| WO | 03103523 | A1 | 12/2003 |
| WO | 2006119972 | A1 | 11/2006 |
| WO | WO-2006119972 | A1 * | 11/2006 .......... A61B 18/203 |
| WO | 2014135511 | A1 | 9/2014 |
| WO | 2014179356 | A1 | 11/2014 |

OTHER PUBLICATIONS

Weiss, Robert A (2013). Noninvasive radio frequency for skin tightening and body contouring. Retrieved Apr. 15, 2021, from https://pubmed.ncbi.nlm.nih.gov/24049924/ (Year: 2013).*

English Translation of International Preliminary Examination Report, Int. Serial No. PCT/EP2015/002396, Int. Filing Date: Nov. 28, 2015, Applicant: Lenicura GmbH, dated Jul. 13, 2017.

Wolkenstein P. et al., Quality of Life Group of the French Society of Dermatology. Quality of life impairment in hidradenitis suppurativa: a study of 61 cases. J Am Acad Dermatol 56:621-3, 2007, Abstract.

Lam J. et al., Hidradenitis suppurativa (acne inversa): management of a recalcitrant disease. Pediatr Dermatol 24:465-73, 2007, Abstract.

Sellheyer K., Krahl D., What causes acne inversa?—the debate continues. J. Cutan Pathol 35:701-3, 2008.

Kurzen H. et al., What causes hidradenitis suppurativa? Exp Dermatol 17:455-72, 2008, Abstract.

Revuz J.E. et al., Prevalence and factors associated with hidradenitis suppurativa: results from two case-control studies. J Am Acad Dermatol 5:596-601, 2008, Abstract.

C. Zouboulis et al., Leitlinie zur Therapie der Hidradenitis suppurativa / Acne inversa, ICD-10-code: L73.2, Stand: Dec. 31, 2012, Abstract.

Jemec G.B., Clinical practice. Hidradenitis suppurativa. N Engl J Med 366:158-64, 2012, Abstract.

German Office Action, German Serial No. 10 2015 000 150.7, Applicant: LeniCura GmbH, dated Feb. 4, 2016.

PCT Notice, Int. Serial No. PCT/EP2015/002396, Int. Filing Date: Nov. 28, 2015, Applicant: Lenicura GmbH, dated Feb. 11, 2016.

International Search Report and Written Opinion, Int Serial No. PCT/EP2015/002396, Int. Filing Date: Nov. 28, 2015, Applicant: Lenicura Gmbh, dated Apr. 26, 2016.

Kamp; S., et al.; Hidradenitis suppurativa: a disease of the absent sebaceous gland? Sebaceous gland number and volume are significantly reduced in uninvolved hair follicles from patients with hidradenitis supparativa; British Journal of Dermatology; Jan. 6, 2011 (6 pages).

Kimball; Alexandra B., et al.; The Comorbidity Burden of Hidradenitis Suppurativa in the United States: A Claims Data Analysis; Dermatol Ther (Heidelb); Oct. 10, 2018 (13 pages); https://doi.org/10.1007/s13555-018-0264-z.

Phan; Kevin, et al.; Hidradenitis suppurativa and acne vulgaris and conglobata—systematic review and meta-analysis; Biomedical Dermatology; Dec. 27, 2019 (7 pages); https://doi.org/10.1186/s41702-019-0045-z.

* cited by examiner

DEVICE AND/OR METHOD FOR TREATING DISEASES OF THE SKIN, GLANDS, MUCOSAE, CONNECTIVE TISSUE, NERVES AND/OR HORNY TISSUE

TECHNICAL FIELD

The present disclosure relates to a device and a method for the treatment of diseases of the skin, glands, mucousae, connective tissue, nerves and/or horny tissue. Furthermore, the disclosure relates to a device and a method for the treatment of hidradenitis suppurativa.

BACKGROUND

Skin disorders can be referred for example to disorders of epidermis, dermis and/or hypodermis (ICD-10-Code L00 to L08). To simplify the attribution, the said diseases and the data in brackets refer to International Statistical Classification of Diseases and Related Health Problems, in short ICD-10. In particular, the said diseases can be triggered by external factors, pathogens, in particular microorganisms, as bacteria and/or fungi, and/or by viruses. Skin lesions, disturbance of the natural acid mantel of the skin und suppressed immune system can provoke pathogens, in particular microorganisms to penetrate the skin and evoke infection, in particular inflammatory or suppurative.

DETAILED DESCRIPTION

This disclosure discusses a device and a method of the treatment of one or a plurality of skin diseases of the group consisting of abscess, furuncle, carbuncle (ICD-10-Code L02), dermatosis, bullous disorders (ICD-10-Code L10-L14), dermatitis, eczema (ICD-10-Code L20-L30), papulosquamous disorders (ICD-10-Code L40-L45), urticaria, erythema (ICD-10-Code L50-54), disorders of skin appendages (ICD-10-Code L60-L75), in particular any form of acne (ICD-10-Code L70), rosacea (ICD-10-Code L71), follicular cysts of skin and subcutaneous tissue (ICD-10-Code L72), other follicular disorders (ICD-10-Code L73), eccrine sweat disorders (ICD-10-Code L74), apocrine sweat disorders (ICD-10-Code L75) and/or other disorders of the skin and subcutaneous tissue (ICD-10-Code L80-L99).

Furthermore, one embodiment of the device and the method as described herein, includes the treatment of skin diseases specific for fetuses and/or newborns (ICD-10-Code P83). In particular, the device and the method according to the disclosure can be adapted for the treatment of sclerema neonatorum (ICD-10-Code P83.0).

In addition, the device and the method as described herein, can be adapted for the treatment of fissures, fistula, abscesses and/or cysts, in particular in anal and/or rectal regions (ICD-10-Code K60-K61). Also, the device and the method as described herein, can be adapted for the treatment of pilonidal cysts (ICD-10-Code L05), dental fistula and/or other fistula tracts.

In particular, one embodiment of the device and the method as described herein, can be adapted for the treatment of inflammatory diseases of joints and/or connective tissue and/or arthropathy (ICD-10-Code M00-M25), in particular inflammatory polyarthritis (ICD-10-Code M05-M14).

The device and the method as described herein, can be designed for the treatment of fibromatosis (ICD-10-Code M72). In particular, the device and the method as described herein, can be adapted for treatment of palma fascia (dupuytren contracture; ICD-10-Code M72.0).

In particular, the device and the method, as described herein, can be adapted for the treatment of one or a plurality of skin diseases of the group consisting of disturbances of skin sensation (ICD-10-Code R20), in particular anesthesia of the skin (ICD-10-Code R20.0) and/or hyposthesia of the skin (ICD-10-Code R20.1), other skin changes, as in particular cyanosis (ICD-10-Code R23.0) and/or spontaneous ecchymosis (ICD-10-Code R23.3).

Hidradenitis suppurativa/acne inversa (also known as akne inversa, pyodermia fistulans significa, acne tetrade) is a common, multifactorial, chronic inflammatory skin disease of terminal hair follicles in skin folds, that leads to significant scarring and impairment, and is associated with an often underestimated heavy burden on patients' quality of life. This and the following information is presented in the S1 guideline for the treatment of hidradenitis suppurativa/acne inversa (C. Zouboulis et al., Leitlinie zur Therapie der Hidradenitis suppurativa/Acne inversa, ICD-10-code: L73.2, Stand: 31.12.2012).

The 1st International Symposium on Hidradenitis suppurativa has formulated the Dessau disease definition (Kurzen H. et al., What causes hidradenitis suppurativa? Exp Dermatol 17:455-72, 2008).

"Hidradenitis suppurativa/acne inversa (HS) is a chronic, inflammatory, recurrent skin disease that usually occurs after puberty and can develop scarring. It manifests itself in painful, deep-seated inflamed lesions in the apocrine gland-bearing areas of the body, most commonly the axillae, inguinal and anogenital regions."

Primary lesions are painful, solitary, deep-seated, cutaneous and subcutaneous nodular formations, which can spontaneously decrease, persist or transform into abscesses. In general, the disease features a horizontal infection of the dermis. Abscesses may merge at depth and rupture spontaneously outwards. The rupture is accompanied by a purulent and/or aqueous-bloody secretion discharge. Hidradenitis suppurativa/acne inversa is not a common acne: the deep-seated areas of the follicle appears to be involved and not the acro-infundibulum as seen with acne vulgaris, which manifests on the convex skin surfaces. For this reason, unlike with acne vulgaris, there are no closed comedones. However, in the early as well as later stages follicular papules and pustules can develop. The inflammatory lesions are initially transient, but gradually they become chronic. It results in the formation of large-scale, partly livid erythematous, nodular, honeycomb-like areas with abscesses and sinus tracts/fistulas with significant fibrosis (hypertrophic scars) and progressive formation of knots. Sinus tracts may also occur in anogenital area. A spontaneous recovery is not to be expected. Substantially, the horizontal dissemination of the disease remains localized in the dermis.

Based on a representative sample of the French population (n=10 000) the prevalence of acne inversa is recorded as 1% (Jemec G. B., Clinical practice. Hidradenitis suppurativa. N Engl J Med 366:158-64, 2012). An earlier study based on clinical evidence report the prevalence of 4% (Revuz J. E. et al., Prevalence and factors associated with hidradenitis suppurativa: results from two case-control studies. J Am Acad Dermatol 5:596-601, 2008).

Despite active research, the pathogenesis of hidradenitis suppurativa/acne inversa is not yet understood. In particular, the chronical nature of the disease is still not determined or not yet agreed upon (Sellheyer K., Krahl D., What causes acne inversa?—the debate continues. J. Cutan Pathol 35:701-3, 2008).

The treatment of hidradenitis suppurativa/acne inversa is often disappointing and imposes a significant burden on the life of people suffering from the disease. In comparison with other skin diseases, Hidradenitis suppurativa/acne inversa has an extremely large impact and considerably reduces the patients' quality of life. (Wolkenstein P. et al., Quality of Life Group of the French Society of Dermatology. Quality of life impairment in hidradenitis suppurativa: a study of 61 cases. J Am Acad Dermatol 56:621-3, 2007). There is no certified medicine for hidradenitis suppurativa/acne inversa.

Local antibiotics cannot cure hidradenitis suppurativa/acne inversa, though often they provide some level of pain and secretion reduction, that brings certain remission. Systemic antibiotics function on the one hand by reducing the follicle's colonization of bacteria, on the other hand they reduce various pro-inflammatory mechanisms. However, they cannot provide a long-lasting cure due to the allergies and resistance, that gradually develop.

At low severity stages, when Hidradenitis suppurativa/acne inversa manifests itself in nodes and abscesses, which can be excised in toto, a primary wound closure can take place. The surgical deroofing of the node and/or sinus by excision with revelation and preservation of the underlying "bottom"-epithelium may be beneficial in some cases and accelerate post-operation wound-healing.

At high severity stages with pronounced findings of confluent abscesses and sinus tracts, a radical excision of the affected tissue up to the apparently non-inflamed fat tissue, sometimes up to the epifascial and if needed, also deeper is the method of choice. Sinus tracts and scars on the borderline and on the bottom of the affected areas should be visualized intraoperatively and be completely removed. A primary wound closure should not be carried out. The close by means of flap plasty is repeatedly described, but carries the risk of infection due to bacterial contamination of the surgical field. Only after radical excision of axillary manifestations, a primary closure can be considered by a flap surgery in the individual case due to the low rate of recurrence per se in this region. (Lam J. et al., Hidradenitis suppurativa (acne inversa): management of a recalcitrant disease. Pediatr Dermatol 24:465-73, 2007).

Therefore, a particular technical object is to provide a device for the treatment of diseases of the skin, glands, mucousae, connective tissue, nerves and/or horny tissue, in particular, Hidradenitis suppurativa (ICD-10-Code L73.2) and/or to provide an effective treatment method, which without dermatolosurgical intervention leads to a better healing process and/or prevention of the symptoms of the diseases, in particular of Hidradenitis suppurativa.

In particular, one solution to this object is to ensure that the device described herein of the said type comprises at least one applicator, which applicator is arranged outside the device housing; that the device comprises at least one radio wave module, which radio wave module is adapted to generate an adjustable electromagnetic radiation with a variable frequency or with at least one constant frequency between 0.1 MHz and 50.0 MHz with an adjustable variable intensity or with at least one adjustable constant intensity between 1.0 J/cm$^3$ and 50.0 J/cm$^3$, in particular between 4.0 J/cm$^3$ and 20.0 J/cm$^3$, and/or with an adjustable constant intensity of 10.0 J/cm$^3$; and that the device is adapted for irradiating a diseased tissue portion, in particular a diseased skin portion, using the at least one applicator emitting electromagnetic radiation generated by the at least one radio wave module.

Another solution to the aforementioned, and the underlying technical problem in particular is that the device described herein of the said type comprises at least one applicator, which applicator is arranged outside a device housing, that the device comprises at least one "IPL-module" (where abbreviation "IPL" means "Intense pulsed light"), which IPL module is adapted to generate an adjustable electromagnetic radiation with a variable or at least one constant wavelength between 400 nm and 1100 nm or with a variable, or at least one constant spectral range between 400 nm and 1100 nm with an adjustable variable or at least one adjustable constant intensity between 1.0 J/cm$^2$ and 40.0 J/cm$^2$, in particular between 5.0 J/cm$^2$ and 30.0 J/cm$^2$, and/or with an adjustable variable or at least one adjustable constant intensity between 4.0 J/cm$^2$ and 20.0 J/cm$^2$, in particular between 10.0 J/cm$^2$ and 20.0 J/cm$^2$; and/or that the device is adapted for irradiating a diseased tissue portion, in particular a diseased skin portion, using the at least one applicator emitting electromagnetic radiation generated by the at least one IPL module.

Furthermore, the device described herein of the said type comprises at least one applicator, which applicator is arranged outside the device housing; that the device comprises at least one radio wave module, which radio wave module is adapted to generate an adjustable electromagnetic radiation with a variable frequency or with at least one constant frequency between 0.1 MHz and 50.0 MHz with an adjustable variable intensity or with at least one adjustable constant intensity between 1.0 J/cm$^3$ and 50.0 J/cm$^3$, in particular between 4.0 J/cm$^3$ and 20.0 J/cm$^3$, and/or with an adjustable constant intensity of 10.0 J/cm$^3$; that the device comprises at least one IPL-module, which IPL-module is adapted to generate an adjustable electromagnetic radiation with a variable or at least one constant wavelength between 400 nm and 1100 nm or with a variable, or at least one constant spectral range between 400 nm and 1100 nm, with an adjustable variable or at least one adjustable constant intensity between 1.0 J/cm$^2$ and 40.0 J/cm$^2$, in particular between 5.0 J/cm$^2$ and 30.0 J/cm$^2$, and/or with an adjustable variable or at least one adjustable constant intensity between 4.0 J/cm$^2$ and 20.0 J/cm$^2$, in particular between 10.0 J/cm$^2$ and 20.0 J/cm$^2$; and/or that the device is adapted for irradiating a diseased tissue portion, in particular a diseased skin portion, using the at least one applicator emitting electromagnetic radiation generated by the at least one radio wave module and the at least one IPL module.

A relevant feature of one embodiment of the device described herein may provide that at least one power source of at least one IPL module and/or at least one radio wave module is arranged in the interior of the device housing and/or that at least one applicator comprises electrodes for generating electromagnetic radiation.

It may be relevant that one or the IPL module of the device described herein comprises at least one light source, at least one xenon flash lamp and/or at least one laser for generating electromagnetic radiation.

In a further relevant aspect of the device, it can be implemented that one or the IPL module, in particular the light source of the IPL module, is arranged in the interior of the device housing. Thus, the size and shape and weight of the applicator can be optimized, namely, the weight and the size can be reduced. As a result, it is possible to make the usage simpler and hence the treatment better.

Furthermore, it can be relevant, that one or the IPL module comprises a cooling device, in particular a cooling device that is arranged in the interior of the device housing. A cooling device can be arranged in the interior of the device housing, operating with cooling water.

In order to transport electromagnetic radiation, generated by the IPL module, in particular through the light source of the IPL module, possibly without loss, in particular caused by dispersion, to at least one applicator, it can be provided, that the device described herein comprises at least one optical waveguide and the electromagnetic radiation generated by one or the IPL module is guided via an optical waveguide to the at least one applicator.

In order to configure the device for irradiating with electromagnetic radiation including or consisting of a variable or one or a plurality of constant wave lengths or of a variable or one or a plurality of constant spectral ranges, it may be relevant, that the device comprises an optical filter or a plurality of optical filters, possibly an optical filter or a plurality of optical filters which is/are configured as an edge filter. Further, it may be relevant, that the device comprises an optical filter or a plurality of optical filters arranged in the interior of the device housing and/or in the at least one applicator, wherein in particular the arrangement of at least one optical filter in the interior of the device housing has a special place-saving embodiment in the device. In particular, it is possible to provide a particular easy-to-operate applicator due to its reduced size and/or reduced weight.

In one aspect, one or the short wavelengths absorption range of one or the optical filter or of a plurality of or the optical filters absorb(s) the portion of light at a value below of at least one wavelength selected from the group consisting of 420 nm, 560 nm, and 690 nm; and/or wherein one or the long wavelengths absorption range of one or the optical filter or of a plurality or all optical filters absorb(s) the portion of light at a value above of a wavelength of 1100 nm.

The device described herein can comprise three optical filters, in particular edge filters, wherein the first optical filter has the short wavelengths absorption range, which absorbs the portion of light at a value below of a wavelength of 420 nm, the second optical filter has the short wavelengths absorption range, which absorbs the portion of light at a value below of a wavelength of 560 nm and the third optical filter has the short wavelengths absorption range, which absorbs the portion of light at a value below of a wavelength of 690 nm.

Furthermore, one or the optical filter or a plurality or the optical filters can have at least one transmission range selected from the group consisting of ranges 420 nm to 1100 nm, 560 nm to 1100 nm, and 690 nm to 1100 nm.

In particular, the cooling water can be configured as an optical filter which in particular has a long wavelengths absorption range that absorbs the portion of light of the wavelength at a value above 1100 nm.

A further, in particular, a place-saving embodiment of the device enables that one or the IPL module and/or one or the radio wave module is/are arranged in the interior of the device housing.

In order to achieve simple handling and ease of operability of the device, it can be provided that the applicator is designed as a hand-held treatment head. Therefore, the IPL module, in particular the light source of the IPL module and/or the radio frequency module are arranged in the interior of the device housing, since the treatment head is designed smaller and lighter as compared to treatment heads of comparable devices.

Another solution to this task discussed herein is achieved by the method for the treatment of the diseases of the skin, glands, mucousae, connective tissue, nerves and/or horny tissue, in particular for the treatment of Hidradenitis suppurativa, through the irradiation of the diseased tissue portion, particularly the diseased skin portion, by electromagnetic radiation with a certain wavelength or at least one certain spectral range with an irradiation interval or several irradiation intervals.

One method discussed herein includes or consists of the treatment in several treatment steps. In three treatment steps, wherein the diseased tissue portion is irradiated in each treatment step with electromagnetic radiation, particularly with a different wavelength or a different spectral range in a certain treatment interval or in several treatment intervals with a variable or at least one constant intensity.

The diseased tissue portion, in particular the diseased skin portion, can be irradiated with electromagnetic radiation at one variable or at least one constant frequency between 0.1 MHz and 50.0 MHz, in particular at a constant frequency of 1.0 MHz, with a variable or at least one constant intensity between 1.0 J/cm$^3$ and 50.0 J/cm$^3$, in particular between 4.0 J/cm$^3$ and 20.0 J/cm$^3$, particularly with constant intensity of 10.0 J/cm$^3$ for at least one irradiation interval between 0.1 seconds and 3.0 seconds, particularly for at least one irradiation interval of 1.0 second.

Moreover, the diseased tissue portion can be irradiated with electromagnetic radiation with a variable wavelength between 400 nm and 1100 nm or at least one constant wavelength between 400 nm and 1100 nm or at least one constant spectral range between 400 nm and 1100 nm, with a variable or at least one constant intensity between 1.0 J/cm$^2$ and 40.0 J/cm$^2$, in particular between 5.0 J/cm$^2$ and 30.0 J/cm$^2$, and/or with one variable or with at least one constant intensity between 4.0 J/cm$^2$ and 20.0 J/cm$^2$, in particular between 10.0 J/cm$^2$ and 20.0 J/cm$^2$, for at least one irradiation interval or more, in particular four, certain irradiation intervals, particularly in an interval or a plurality of irradiation intervals between 1 ms and 50 ms in each case, in particular between 2 ms and 20 ms in each case, particularly of 8 ms each, wherein treatment irradiation pauses of between 1 ms and 50 ms are respected between the irradiation intervals in each case, in particular of between 2 ms and 20 ms in each case, particularly of 8 ms each.

Furthermore one embodiment of the disclosure may provide that the diseased tissue portion, in particular the diseased skin portion, is irradiated with electromagnetic radiation at one variable or at least one constant frequency between 0.1 MHz and 50.0 MHz, in particular at a constant frequency of 1.0 MHz, with a variable or at least one constant intensity between 1.0 J/cm$^3$ and 50.0 J/cm$^3$, in particular between 4.0 J/cm$^3$ and 20.0 J/cm$^3$, particularly with constant intensity of 10.0 J/cm$^3$ for at least one irradiation interval between 0.1 seconds and 3.0 seconds, particularly for at least one irradiation interval of 1.0 second; and that the diseased tissue portion is irradiated with electromagnetic radiation with a variable wavelength between 400 nm and 1100 nm or at least one constant wavelength between 400 nm and 1100 nm or at least one constant spectral range between 400 nm and 1100 nm, with a variable or at least one constant intensity between 1.0 J/cm$^2$ and 40.0 J/cm$^2$, in particular between 5.0 J/cm$^2$ and 30.0 J/cm$^2$, and/or with one variable or with at least one constant intensity between 4.0 J/cm$^2$ and 20.0 J/cm$^2$, in particular between 10.0 J/cm$^2$ and 20.0 J/cm$^2$, for at least one irradiation interval or a plurality of, in particular four, certain irradiation intervals, particularly in an interval or a plurality of irradiation intervals between 1 ms and 50 ms in each case, in particular between 2 ms and 20 ms in each case, particularly of 8 ms each, wherein treatment irradiation pauses of between 1 ms and 50 ms are respected between the irradiation intervals in each case, in particular of between 2 ms and 20 ms in each case, particularly of 8 ms each.

A specific embodiment of the method described hereinfor the treatment of the diseases of the skin, glands, mucousae, connective tissue, nerves and/or horny tissue, in particular Hidradenitis suppurativa may include or consist of at least three treatment steps, wherein the diseased tissue portion, in particular the skin portion, in a first treatment is irradiated in 4 irradiation intervals between 1 ms and 50 ms in each case, in particular between 2 ms and 20 ms in each case, particularly of 8 ms each, with an electromagnetic radiation of a spectral range between 400 nm and 1100 nm, with an intensity between 1.0 J/cm$^2$ and 40.0 J/cm$^2$ in each case, in particular between 5.0 J/cm$^2$ and 30.0 J/cm$^2$, and/or between 4.0 J/cm$^2$ and 20.0 J/cm$^2$, in particular between 10.0 J/cm$^2$ and 20.0 J/cm$^2$, wherein a treatment pause of between 1 ms and 50 ms is respected between the irradiation intervals in each case, in particular of between 2 ms and 20 ms in each case, particularly of 8 ms, and wherein simultaneously and/or subsequently the diseased tissue portion, in particular the skin portion, is irradiated during at least one irradiation interval between 0.1 seconds and 3.0 seconds, in particular of 1 second, at a constant frequency between 0.1 MHz and 50.0 MHz, in particular at a constant frequency of 1.0 MHz, with an intensity between 1.0 J/cm$^3$ and 50.0 J/cm$^3$, in particular between 4.0 J/cm$^3$ and 20.0 J/cm$^3$, in particular with an intensity of 10.0 J/cm$^3$; wherein in a second treatment step the diseased tissue portion, in particular the skin portion, is treated in 4 irradiation intervals between 1 ms and 50 ms in each case, in particular between 2 ms and 20 ms in each case, particularly of 8 ms each, with an electromagnetic radiation of a spectral range between 560 nm and 1100 nm, with an intensity between 1.0 J/cm$^2$ and 40.0 J/cm$^2$ in each case, in particular between 5.0 J/cm$^2$ and 30.0 J/cm$^2$, and/or between 4.0 J/cm$^2$ and 20.0 J/cm$^2$, in particular between 10.0 J/cm$^2$ and 20.0 J/cm$^2$, wherein a treatment pause of between 1 ms and 50 ms is respected between the irradiation intervals in each case, in particular of between 2 ms and 20 ms in each case, particularly of 8 ms, and wherein simultaneously and/or subsequently the diseased tissue portion, in particular the skin portion, is irradiated during at least one irradiation interval between 0.1 seconds and 3.0 seconds, in particular of 1.0 seconds, at a constant frequency between 0.1 MHz and 50.0 MHz, in particular at a constant frequency of 1.0 MHz, with an intensity between 1.0 J/cm$^3$ and 50.0 J/cm$^3$, in particular between 4.0 J/cm$^3$ and 20.0 J/cm$^3$, in particular with an intensity of 10.0 J/cm$^3$; and wherein in a third treatment step the diseased tissue portion, in particular the skin portion, is treated in 4 irradiation intervals between 1 ms and 50 ms in each case, in particular between 2 ms and 20 ms in each case, particularly of 8 ms each, with an electromagnetic radiation of a spectral range between 690 nm and 1100 nm, with an intensity between 1.0 J/cm$^2$ and 40.0 J/cm$^2$ in each case, in particular between 5.0 J/cm$^2$ and 30.0 J/cm$^2$, and/or between 4.0 J/cm$^2$ and 20.0 J/cm$^2$, in particular between 10.0 J/cm$^2$ and 20.0 J/cm$^2$, wherein a treatment pause of between 1 ms and 50 ms is respected between the irradiation intervals in each case, in particular of between 2 ms and 20 ms in each case, particularly of 8 ms, and wherein simultaneously and/or subsequently the diseased tissue portion, in particular the skin portion, is irradiated during at least one irradiation interval between 0.1 seconds and 3.0 seconds, in particular of 1.0 seconds, at a constant frequency between 0.1 MHz and 50.0 MHz, in particular at a constant frequency of 1.0 MHz, with an intensity between 1.0 J/cm$^3$ and 50.0 J/cm$^3$, in particular between 4.0 J/cm$^3$ and 20.0 J/cm$^3$, in particular with an intensity of 10.0 J/cm$^3$.

In particular, the method for the treatment of the diseases of the skin, glands, mucousae, connective tissue, nerves and/or horny tissue, in particular Hidradenitis suppurativa is performed using the device as described herein.

These and further embodiments are disclosed in the claims, the accompanying figures and the related description of the figures.

The term "treatment" as used herein may refer to the treatment of humans. In addition, the treatment of an animal, in particular of a mammal, may also be meant.

The wording "adapted for" may as well be understood as "programmed for" in the context of the present application. In particular, the device as described herein may be programmed to perform the method as described herein.

The above disclosure will now be explained in more detail by way of several examples.

Figure 1:
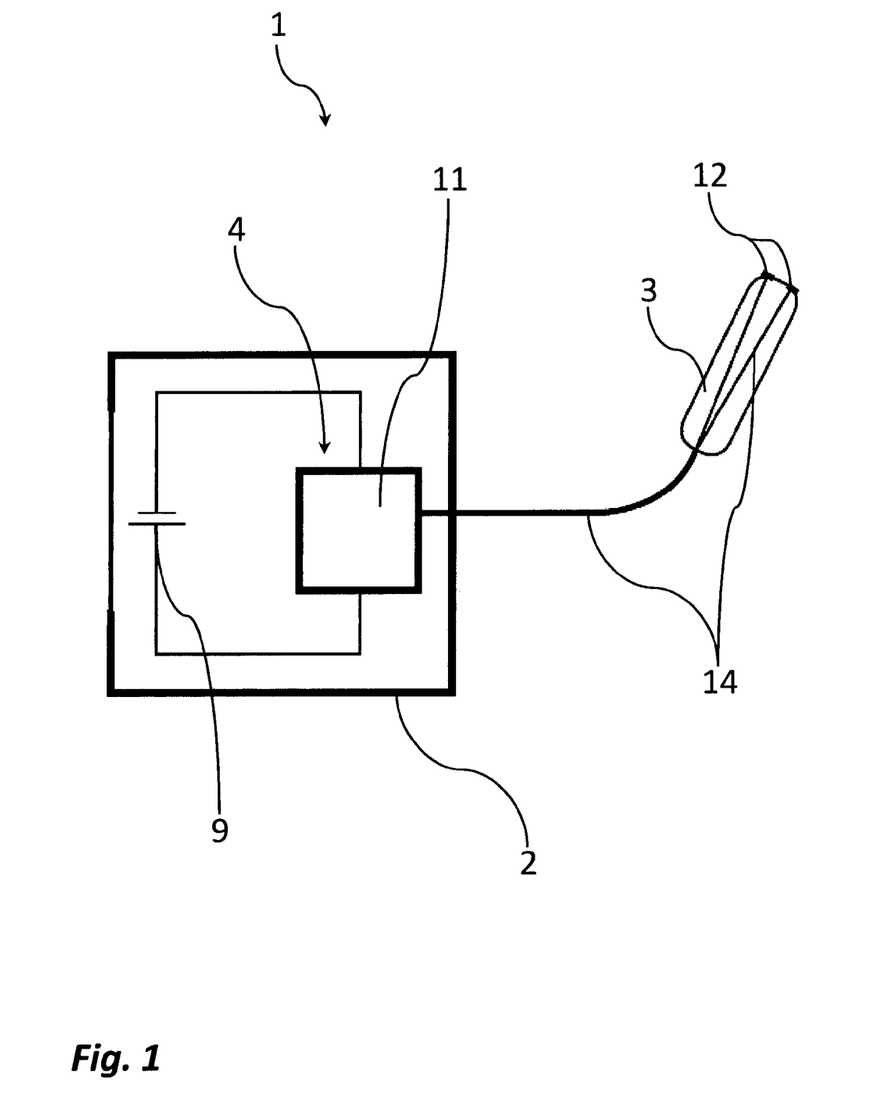
FIG. 1 illustrates schematically one embodiment of the device for the treatment of diseases of the skin, glands, mucousae, connective tissue, nerves and/or horny tissue, in particular, Hidradenitis suppurativa.
Figure 2:
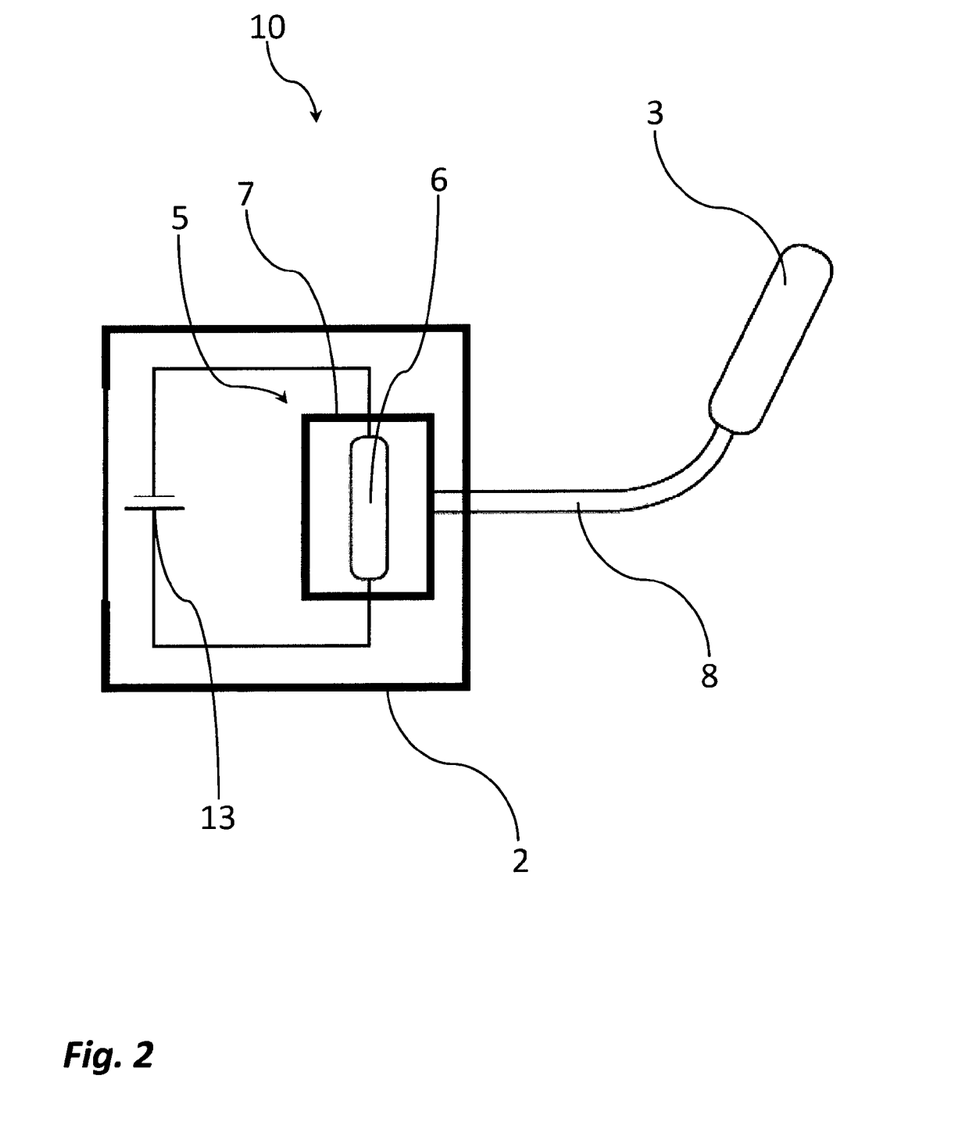
FIG. 2 illustrates another embodiment of the device for the treatment of diseases of the skin, glands, mucousae, connective tissue, nerves and/or horny tissue, in particular, Hidradenitis suppurativa.
Figure 3:
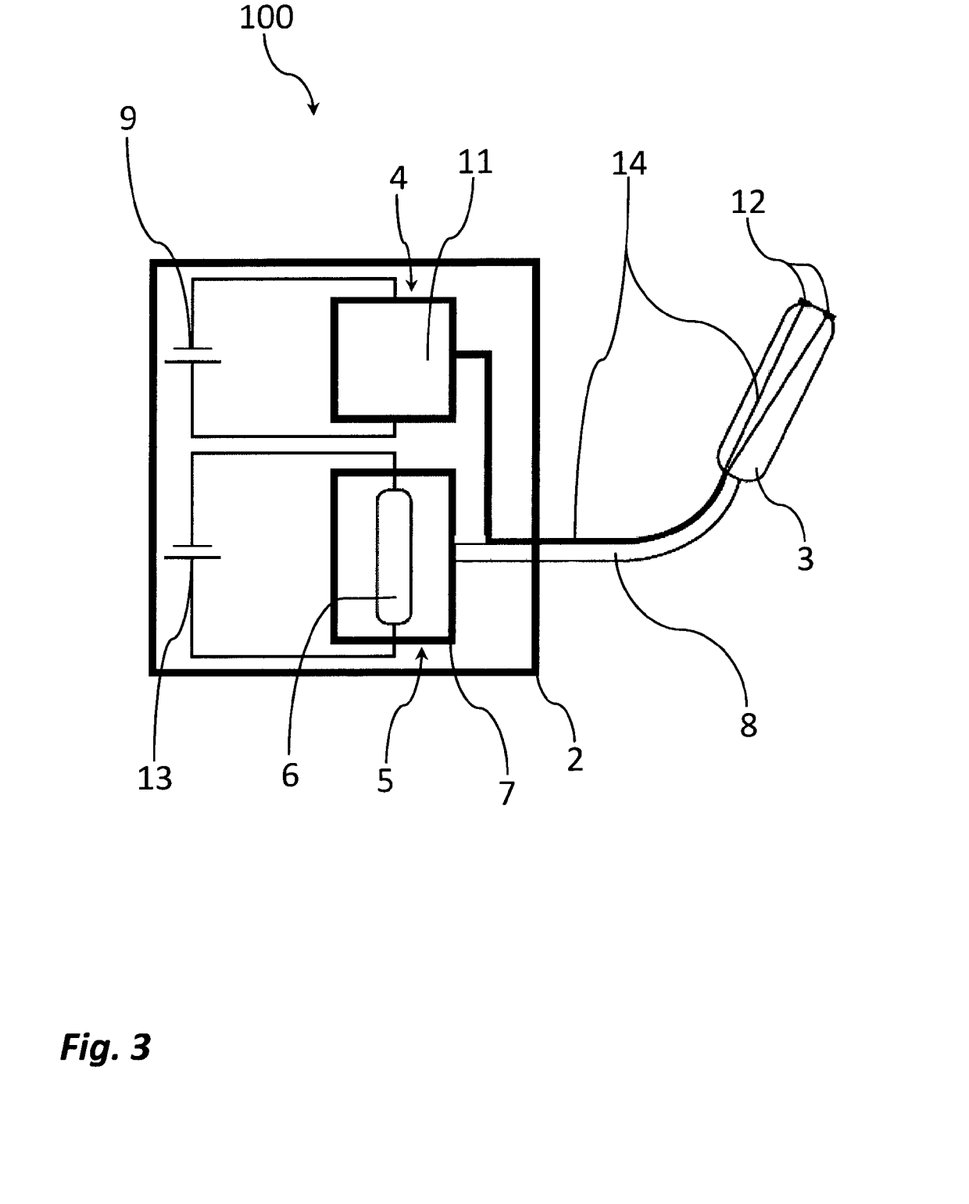
FIG. 3 illustrates yet another, combined embodiment of the device for the treatment of diseases of the skin, glands, mucousae, connective tissue, nerves and/or horny tissue, in particular, Hidradenitis suppurativa.

FIGS. 1 to 3 illustrate several differently configured examples of the device for the treatment of diseases of the skin, glands, mucousae, connective tissue, nerves and/or horny tissue, in particular, Hidradenitis suppurativa, which are denoted by 1, 10, and 100 in their entirety.

FIG. 1 and FIG. 3 show examples of embodiments of the device 1, 100 for the treatment of diseases of the skin, glands, mucousae, connective tissue, nerves and/or horny tissue, in particular, Hidradenitis suppurativa, each comprises a device housing 2 with a radio wave module 4 arranged in the interior thereof. Each radio wave module 4 comprises at least one frequency generator 11 and a power supply 9 to power at least one frequency generator 11.

The device 1, 100 of the disclosure comprises an applicator 3 designed as a hand-held treatment head, which applicator 3 is arranged outside of the device housing 2. On or in the applicator 3 there are at least two applicator electrodes 12, which are connected to the radio wave module 4 through at least one power supply cable 14, that is particularly arranged in the interior of the applicator 3.

The device 1, 100 is programmed in such a way that through the applicator 3 respectively through at least two applicator electrodes 12 a portion of the diseased tissue, in particular a diseased skin portion, can be irradiated with electromagnetic radiation generated in the radio wave module 4.

The radio wave module 4 of the device 1, 100 of the disclosure is adapted to generate an adjustable electromagnetic radiation with a variable frequency or with at least one constant frequency between 0.1 MHz and 50.0 MHz with an adjustable variable intensity or with at least one adjustable constant intensity between 1.0 J/cm$^3$ and 50.0 J/cm$^3$, in particular between 4.0 J/cm$^3$ and 20.0 J/cm$^3$, and/or with an adjustable constant intensity of 10.0 J/cm$^3$.

FIG. 2 schematically shows a further embodiment of the device 10 of the disclosure for the treatment of diseases of the skin, glands, mucousae, connective tissue, nerves and/or horny tissue, in particular, Hidradenitis suppurativa.

The embodiments of the devices 10, 100 as shown in FIGS. 2 and 3 each comprise a device housing 2 with an IPL module 5 arranged in the interior thereof. In each case, IPL module 5 comprises at least one light source 6, a cooling device 7 and one or more power supply units 13 to power the at least one light source 6 and/or the cooling device 7. It may furthermore be relevant for the device 100 of the disclosure to have only one shared power supply unit 9, 13 for the radio wave module 4 and the IPL module 5.

The device 10, 100 comprises an applicator 3 configured as hand-held treatment head, which applicator 3 is arranged outside the device housing 2. The applicator 3 is connected with the IPL module 5 through the light waveguide 8 and wherein the electromagnetic radiation generated by IPL module is guided to the applicator 3, in such a way that the device 10, 100 of the disclosure is adapted so that the applicator 3 can irradiate a diseases tissue portion, in particular a diseased skin portion, with electromagnetic radiation generated by at least one IPL module 5 using at least one applicator.

The IPL module 5 of the device 10, 100 is adapted to generate an adjustable electromagnetic radiation with a variable or at least one constant wavelength between 400 nm and 1100 nm or with a variable, or at least one constant spectral range between 400 nm and 1100 nm with an adjustable variable or at least one adjustable constant intensity between 1.0 J/cm² and 40.0 J/cm², in particular between 5.0 J/cm² and 30.0 J/cm², and/or with an adjustable variable or at least one adjustable constant intensity between 4.0 J/cm² and 20.0 J/cm², in particular between 10.0 J/cm² and 20.0 J/cm².

The cooling device 7 of the IPL module 5 is designed as a cooling device operating with cooling water 7.

In order to configure a certain wavelength or a certain spectral range for irradiating a diseased tissue portion, in particular a diseased skin portion, the device 10, 100 comprises one or a plurality of optical filters (not shown). One or a plurality of the optical filters is/are optionally configured as an edge filter and arranged in the interior of the device housing 2, wherein one or the short wavelengths absorption range of one or the optical filter or of a plurality of or the optical filters absorb(s) the portion of light at a value below of at least one wavelength selected from the group consisting of 420 nm, 560 nm, and 690 nm; and/or wherein one or the long wavelengths absorption range of one or the optical filter or of a plurality or all optical filters absorb(s) the portion of light at a value above a wavelength of 1100 nm. In particular, the optical filter(s) of the device 10, 100 is/are configured so that the optical filter(s) has/have at least one transmission range selected from the group consisting of ranges 420 nm to 1100 nm, 560 nm to 1100 nm, and 690 nm to 1100 nm. In the illustrated embodiment of the device 10, 100 it is provided that the cooling water of the cooling device 7 is configured as an optical filter which in particular has a long wavelengths absorption range that absorbs the portion of light of the wavelength at a value above 1100 nm.

FIG. 1 to FIG. 3 illustrate examples of the device 1, 10, 100 which may not comprise a cooling device intended for skin.

The invention claimed is:

1. A method for the treatment of a diseased tissue portion of at least one of the skin, glands, mucousae, connective tissue, or nerves, including irradiating the diseased tissue portion by electromagnetic radiation with a wavelength or at least one spectral range with one or more irradiation intervals, wherein the diseased tissue portion is irradiated at a variable frequency between 0.1 MHz and 50.0 MHz or at least one constant frequency between 0.1 MHz and 50.0 MHz, with an adjustable variable intensity between 10.0 J/cm³ and 50.0 J/cm³ or at least one adjustable constant intensity between 10.0 J/cm³ and 50.0 J/cm³, wherein the treatment comprises at least three treatment steps;

wherein in a first treatment step the diseased tissue portion is irradiated in 4 irradiation intervals between 1 ms and 50 ms each, with an electromagnetic radiation or a spectral range between 400 nm and 1100 nm, with an intensity between 1.0 J/cm² and 40.0 J/cm² each, wherein a treatment pause of between 1 ms and 50 ms is respected between the irradiation intervals, and wherein simultaneously or subsequently the diseased tissue portion is irradiated during at least one irradiation interval between 0.1 seconds and 3.0 seconds, at the at least one constant frequency between 0.1 MHz and 50.0 MHz, with the adjustable variable intensity or with the at least one adjustable constant intensity between 10.0 J/cm³ and 50.0 J/cm³, wherein in a second treatment step the diseased tissue portion is treated in 4 irradiation intervals between 1 ms and 50 ms each, with an electromagnetic radiation or a spectral range between 560 nm and 1100 nm, with an intensity between 1.0 J/cm² and 40.0 J/cm² each, wherein a treatment pause of between 1 ms and 50 ms is respected between the irradiation intervals, and wherein simultaneously or subsequently the diseased tissue portion is irradiated during at least one irradiation interval between 0.1 seconds and 3.0 seconds, at the at least one constant frequency between 0.1 MHz and 50.0 MHz, with the adjustable variable intensity or with the at least one adjustable constant intensity between 10.0 J/cm³ and 50.0 J/cm³; and wherein in a third treatment step the diseased tissue portion is treated in 4 irradiation intervals between 1 ms and 50 ms each, with an electromagnetic radiation for a spectral range between 690 nm and 1100 nm, with an intensity between 1.0 J/cm² and 40.0 J/cm² each, wherein a treatment pause of between 1 ms and 50 ms is respected between the irradiation intervals, and wherein simultaneously or subsequently the diseased tissue portion is irradiated during at least one irradiation interval between 0.1 seconds and 3.0 seconds, at the at least one constant frequency between 0.1 MHz and 50.0 MHz, with the adjustable variable intensity or with the at least one adjustable constant intensity between 10.0 J/cm³ and 50.0 J/cm³;

wherein the method is carried out using a device, comprising:
a device housing;
at least one applicator arranged outside the device housing;
at least one radio frequency (RF) module arranged inside the device housing and adapted to generate an adjustable electromagnetic radiation with a variable frequency between 0.1 MHz and 50.0 MHz or at least one constant frequency between 0.1 MHz and 50.0 MHz, with an adjustable variable intensity between 10.0 J/cm³ and 50.0 J/cm³ or at least one adjustable constant intensity between 10.0 J/cm³ and 50.0 J/cm³; and
at least one intense pulsed light (IPL) module arranged inside the device housing and including at least one light source adapted to generate an adjustable electromagnetic radiation with a variable wavelength between 400 nm and 1100 nm or at least one constant wavelength between 400 nm and 1100 nm, or with a variable spectral range between 400 nm and 1100 nm or at least one constant spectral range between 400 nm and 1100 nm, and with an adjustable variable intensity between 1.0 J/cm$^2$ and 40.0 J/cm$^2$ or at least one adjustable constant intensity between 1.0 J/cm$^2$ and 40.0 J/cm$^2$, wherein the device is adapted for irradiating the diseased tissue portion using the at least one applicator emitting electromagnetic radiation generated by the at least one RF module and emitting electromagnetic radiation generated by the at least one IPL module.

2. The method as claimed in claim 1, including treating disorders of epidermis, dermis and hypodermis caused by bacteria or fungi or viruses.

3. The method as claimed in claim 1, including treating suppurative diseases of the skin, glands, mucousae, connective tissue, nerves or horny tissue, or treating diseases of the group consisting of anesthesia of the skin, hyposthesia of the skin, cyanosis, and spontaneous ecchymosis.

4. The method as claimed in claim 1, including treating skin diseases including abscess, furuncle, carbuncle, dermatosis, bullous disorders, dermatitis, eczema, papulosquamous disorders, urticaria, erythema, disorders of skin appendages, any form of acne, rosacea, follicular cysts of skin and subcutaneous tissue, other follicular disorders, eccrine sweat disorders, apocrine sweat disorders, or other disorders of the skin and subcutaneous tissue.

5. The method as claimed in claim 1, including treating skin diseases specific for fetuses or newborns, including sclerema neonatorum.

6. The method as claimed in claim 1, including treating fissures, fistula, abscesses or cysts, including in the anal or rectal region, and including treating the pilonidal cyst, dental fistula or other fistula tract.

7. The method as claimed in claim 1, including treating inflammatory diseases of joints or connective tissue.

8. The method as claimed in claim 1, including treating diseases in joints and connective tissue caused by bacteria and/or fungi or viruses.

9. The method as claimed in claim 1, including treating arthropathy, including inflammatory polyarthritis or fibromatosis or palma fascia/dupuytren contracture.

10. The method as claimed in claim 1, wherein the device also comprises one or more optical filters arranged inside the device housing, wherein a short wavelength absorption range of the filter(s) absorbs a portion of light at a value below a wavelength of 420 nm, and wherein a long wavelength absorption range of the filter(s) absorbs a portion of light at a value above a wavelength of 1100 nm, such that the filter(s) has a transmission range of 420 nm to 1100 nm.

11. The method as claimed in claim 10, wherein the filter(s) comprise three optical edge filters comprising: a first optical edge filter that absorbs a portion of light at a value below of a wavelength of 420 nm; a second optical edge filter that absorbs a portion of light at a value below of a wavelength of 560 nm; and a third optical edge filter that absorbs a portion of light at a value below of a wavelength of 690 nm.

12. The method as claimed in claim 1, wherein the device also comprises a cooling device arranged in the interior of the device housing and operated with cooling water, which is configured as an optical filter that absorbs a portion of light of at a value above a wavelength of 1100 nm.

13. A method for treatment of hidradenitis suppurativa or abscesses, including using a device comprising a device housing, at least one applicator arranged outside the device housing, at least one radio wave module adapted to generate an adjustable electromagnetic radiation with a variable frequency between 0.1 MHz and 50.0 MHz or with at least one constant frequency between 0.1 MHz and 50.0 MHz and with an adjustable variable intensity between 4.0 J/cm$^3$ and 50.0 J/cm$^3$ or with at least one adjustable constant intensity between 4.0 J/cm$^3$ and 50.0 J/cm$^3$ wherein the device is adapted for irradiating a diseased tissue portion resulting from hidradenitis suppurativa or at least one abscess using the at least one applicator emitting electromagnetic radiation generated by the at least one radio wave module with a wavelength or at least one spectral range with one or more irradiation intervals, wherein the diseased tissue portion resulting from hidradenitis suppurativa or at least one abscess is irradiated at a variable frequency between 0.1 MHz and 50.0 MHz or at least one constant frequency between 0.1 MHz and 50.0 MHz, with an adjustable variable intensity between 4.0 J/cm$^3$ and 50.0 J/cm$^3$ or with at least one adjustable constant intensity between 4.0 J/cm$^3$ and 50.0 J/cm$^3$.

\* \* \* \* \*